Figure 1:
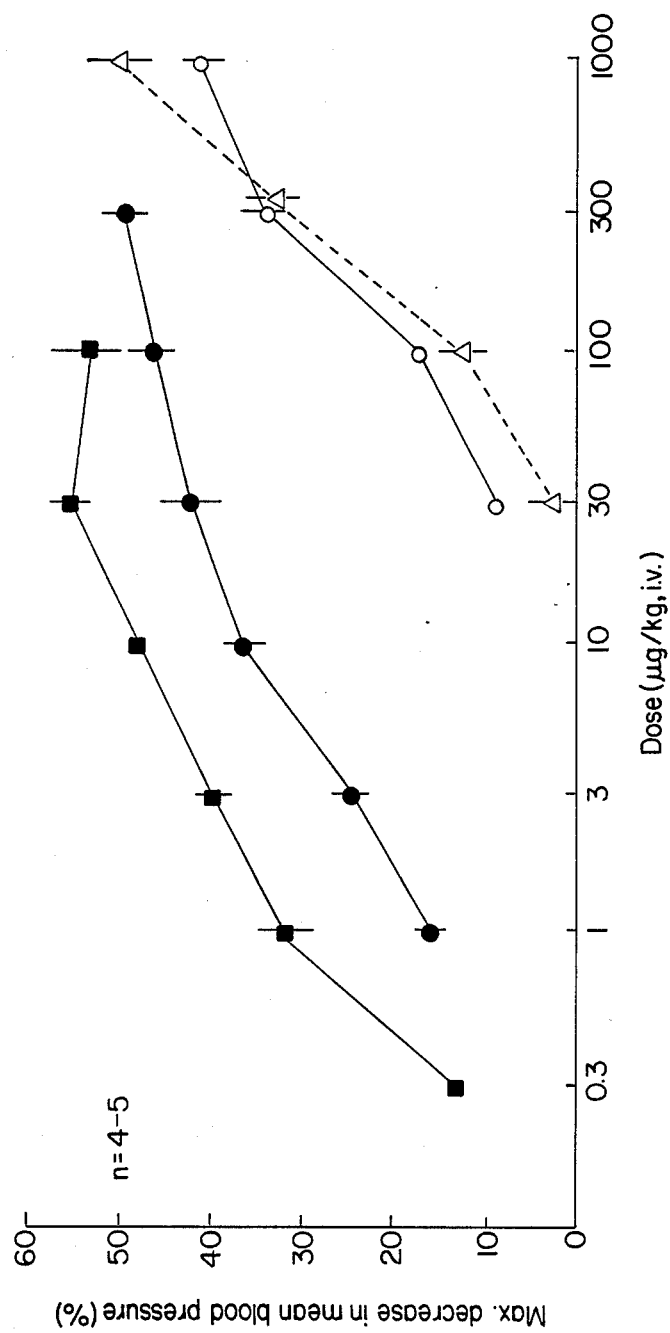

United States Patent [19]

Kunii et al.

[11] Patent Number: 4,794,118
[45] Date of Patent: Dec. 27, 1988

[54] 1,4-BENZODIOXANE DERIVATIVES

[75] Inventors: Toshinobu Kunii; Norio Minami; Fumihiro Ozaki; Nobuyuki Mori; Mikio Takeda; Hiroshi Katoh, all of Ibaraki, Japan

[73] Assignee: Eisai Co., Ltd., Tokyo, Japan

[21] Appl. No.: 887,720

[22] Filed: Jul. 18, 1986

[30] Foreign Application Priority Data

Jul. 23, 1985 [JP] Japan .................. 60-161096

[51] Int. Cl.⁴ .................. A61K 31/335; C07D 319/20; C07D 405/12; C07D 413/12
[52] U.S. Cl. .................. 514/452; 549/366; 546/270; 544/148; 514/338; 514/232.5; 514/233.8
[58] Field of Search .............. 549/366; 514/452, 338, 514/237; 546/270; 544/148

[56] References Cited

U.S. PATENT DOCUMENTS 3,101,345 8/1963 Schmidt et al. .................. 549/364

Primary Examiner—Nicky Chan
Attorney, Agent, or Firm—Wenderoth, Lind & Ponack

[57] ABSTRACT

1,4-Benzodioxane derivatives represented by the following general formula:

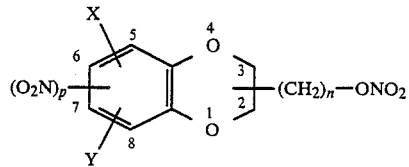

wherein p stands for an integer of 0-2, X and Y are same or different, and each represent a hydrogen atom; or a group represented by the formula —OR in which R denotes a hydrogen atom, a lower alkyl, lower alkoxycarbonyl or acyl group, or a group represented by the formula

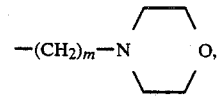

m being an integer of 1 or 2; cyano group; or carboxy group, n is an integer of 1-3, exclusive of the case wherein p=0 and X=Y=H, or a pharmacologically acceptable salt thereof. Their process for the preparation, their use as therpeutic and/or preventive compositions for ischemic heart diseases and heart failure and their application for the control of blood pressure during surgical operations are also described.

10 Claims, 2 Drawing Sheets

1,4-BENZODIOXANE DERIVATIVES

This invention relates to 1,4-benzodioxane derivatives having excellent effects as medicines. More specifically, the present invention is concerned with 1,4-benzodioxane derivatives represented by the following general formula (I):

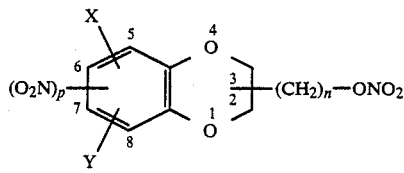

wherein p stands for an integer of 0–2, X and Y are same or different, and each represent a hydrogen atom; or a group represented by the formula —OR in which R denotes a hydrogen atom, a lower alkyl, lower alkoxycarbonyl or acyl group, or a group represented by the formula

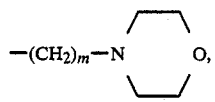

m being an integer of 1 or 2; cyano group; or carboxy group, n is an integer of 1–3, exclusive of the case wherein p=0 and X=Y=H, or a pharmacologically acceptable salt thereof; their processes for the preparation thereof; and medicines containing same.

In the above general formula (I), the term "lower alkyl group" as used in the definition for R means straight-chain or branched alkyl groups having 1–6 carbon atoms, for example, alkyl groups such as methyl, ethyl, n-propyl, isopropyl, n-butyl, isobutyl, 1-methylpropyl, tert-butyl, n-pentyl, 1-ethylpropyl, isoamyl and n-hexyl. By the term "lower alkoxy" as used in the term "lower alkoxycarbonyl group", is meant those derived from the above-described lower alkyl groups.

As illustrative examples of the acyl group, may be mentioned acyl groups derived from aliphatic monocarboxylic acids having 1–6 carbon atoms such as formyl, acetyl, propionyl, butyryl, isobutyryl, valeryl, isovaleryl, pivaloyl and hexanoyl, acyl groups derived from heterocyclic carboxylic acids such as nicotinoyl group, and so on.

When R means a hydrogen atom, the compounds (I) of this invention may be provided as their salts including, for example, their alkali metal and alkaline earth metal salts such as their Na, K and Ca salts and their organic base salts such as their ethanolamine salts. Needless to say, these salts are embraced in the present invention.

Certain compounds in this invention may also be converted into pharmacologically acceptable salts, for example, their inorganic acid addition salts such as their hydrochlorides, hydrobromides and hydroiodides and their organic acid addition salts such as their maleates, fumarates, succinates, malonates, acetates, citrates and methanesulfonates.

Nitrite base medicines led by nitroglycerin (hereinafter abbreviated merely as "NG") have been used more than 100 years. They are still considered to be effective medicines for angina pectoris even now. In the meantime, isosorbide dinitrate (hereinafter abbreviated merely as "ISDN") and the like have been developed to date.

Although the mechanism of effects of such a nitrite base medicine has not been fully elucidated, the following theory is considered to be most cogent. Namely, the nitride base medicine causes veins to expand so that endovenous pool is allowed to take place. As a result, the intravenous perfusion rate is reduced and the blood pressure in the final stage of diastole of the left ventricle is hence reduced. The tension of the left ventricle is therefore reduced, leading to a reduction in the intramyocardinal oxygen consumption.

Under the above-mentioned circumstances, the present inventors have proceeded for many years with an extensive investigation in order to develop compounds which are nitro-containing agents different from conventional NG and ISDN preparation and have stronger activities than these conventional medicines. As a result, it has now been found that compounds having the below-described structural formula can achieve the above object.

Namely, the compounds of this invention are 1,4-benzodioxane derivatives represented by the following general formula:

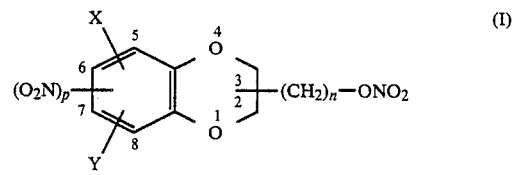

wherein p stands for an integer of 0–2, X and Y are same or different, and each represent a hydrogen atom; or a group represented by the formula —OR in which R denotes a hydrogen atom, a lower alkyl, lower alkoxycarbonyl or acyl group, or a group represented by the formula

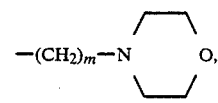

m being an integer of 1 or 2; cyano group; or carboxy group, n is an integer of 1–3, exclusive of the case wherein p=0 and X=Y=H, or a pharmacologically acceptable salt thereof.

The above-described compounds of this invention have advantageous features such as those described below:

(1) They have strong vasodilative effects on coronary arteries, peripheral arterial vessels and peripheral venous vessels. Thus, in addition to increasing coronary blood flow, they have advantageous action of reducing both pre- and post-loads to the heart. In this regard, their actions are more potent than those of NG and ISDN.

(2) They cause vasodilation at both intravenous and intraduodenal administration, indicating good absorption from the gastrointestinal system.

(3) They have higher $LD_{50}$ values than NG in mice and hence have wide safety margins. They cause extremely reduced formation of methemoglobin than NG.

Where R stands for a hydrogen atom in the compounds (I) of this invention, it is possible to increase their solubility, for example, by converting them into sodium salts. Further, nitro-containing compounds tends to adhere to transfusion equipment upon their drip infusion and develop trouble frequently. The compounds of this invention are however less sticky compared with conventional nitro-containing compounds and are also advantageous in this respect.

The diseases to which the compounds of this invention can be applied as medicines include heart failure and ischemic heart diseases as typified by a variety of angina pectoris (effort angina, angina at rest, variant angina etc.).

They can be also useful for the control of blood pressure during surgical operations.

Obejcts of this invention are to provide the novel 1,4-benzodioxane derivatives effective for ischemic heart diseases, heart failure and blood pressure control during an operation, their preparation process, and medicinal compositions which contain these compounds as effective ingredients for the above-mentioned diseases.

The above and other objects, features and advantages of this invention will become apparent from the following description and the appended claims, taken in conjunction with the accompanying drawings.

A variety of routes may be contemplated for the preparation of the compounds of this invention. Of these, certain representative routes will hereinafter be described specifically in detail.

Preparation Route 1:

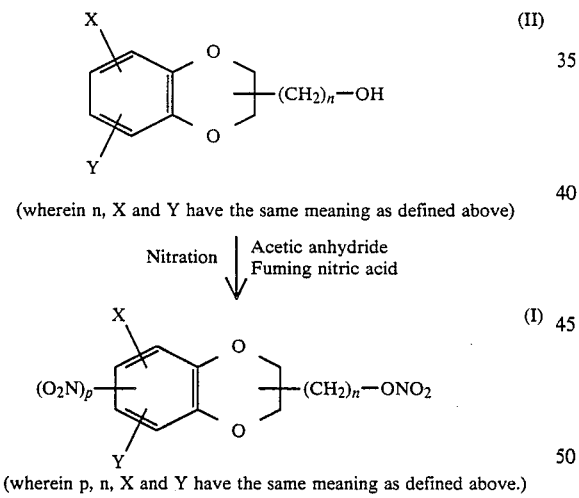

(wherein n, X and Y have the same meaning as defined above)

(wherein p, n, X and Y have the same meaning as defined above.)

Namely, the compound represented by the formula (II) is chosen as a starting material. It is nitrated by a method known per se in the art to prepare the desired product (I). For its nitration, it is reacted in the presence or absence of a solvent by using a nitrating agent such as acetic anhydride-fuming nitric acid, fuming nitric acid or fuming nitric acid-conc. sulfuric acid. This reaction is usually conducted at about 0°–40° C. and as a solvent, acetonitrile, chloroform, dichloromethane, acetic acid or the like is preferred.

By the above reaction, various desired products are formed as a mixture depending on the degree of nitration (p=0−2). These desired products are then isolated and purified, for example, by silica gel chromatography or the like, so that one of the desired product can be obtained.

Where Y is a hydroxyl group bonded to the 8-position, —(CH$_2$)OH is bonded to the 2-position, X=H and n=1, the starting material, namely, 8-hydroxy-2-hydroxymethyl-1,4-benzodioxane represented by the following structural formula (III) has already been disclosed, for example, in U.S. Pat. No. 3,101,345.

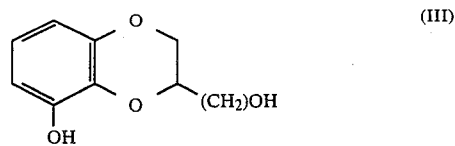

It can be prepared by the process described in the above patent. Namely, it can be obtained by reacting pyrogallol with epichlorohydrin.

A description will next be made particularly of the preparation of 8-hydroxy-2-nitratomethyl-7-nitro-1,4-benzodioxane which is a representative compound according to the present invention. Its preparation is shown by the following reaction formula:

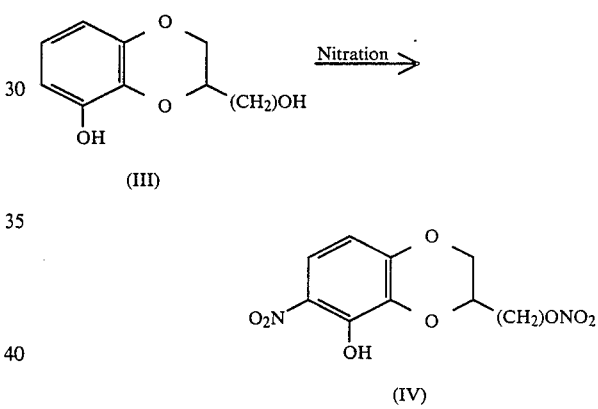

Preparation Route 2:

This preparation route is suitable for the preparation of certain 1,4-benzodioxane derivatives of the general formula (I) in which Y is represented by the formula —OR and R has the same meaning as defined above.

Although they may also be prepared by Preparation Route 1, it is possible to obtain them with ease by the following route.

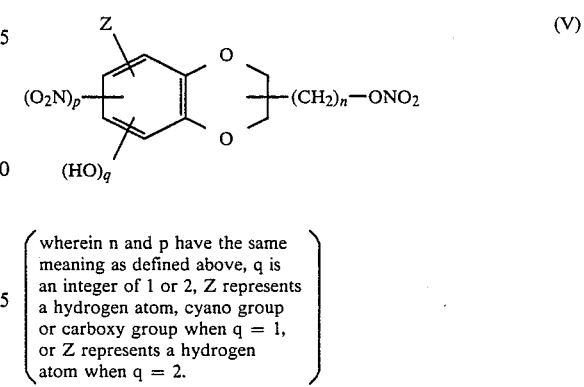

(wherein n and p have the same meaning as defined above, q is an integer of 1 or 2, Z represents a hydrogen atom, cyano group or carboxy group when q = 1, or Z represents a hydrogen atom when q = 2.)

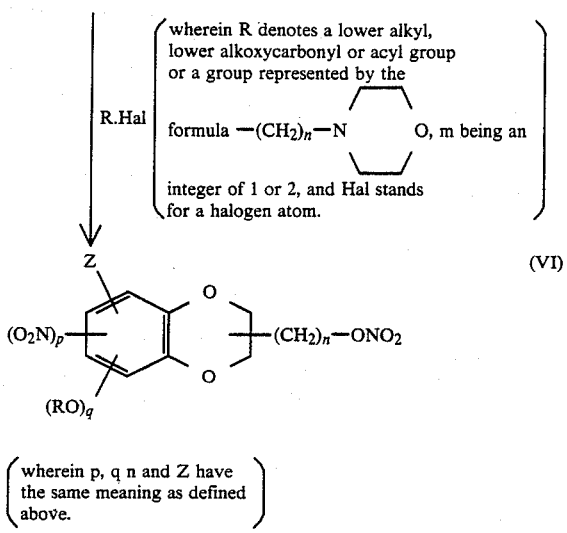

$$\begin{Bmatrix} \text{wherein R denotes a lower alkyl,} \\ \text{lower alkoxycarbonyl or acyl group} \\ \text{or a group represented by the} \\ \text{formula} -(CH_2)_n-N\diagup\diagdown O, \text{ m being an} \\ \text{integer of 1 or 2, and Hal stands} \\ \text{for a halogen atom.} \end{Bmatrix}$$

(VI)

$\begin{pmatrix} \text{wherein p, q n and Z have} \\ \text{the same meaning as defined} \\ \text{above.} \end{pmatrix}$ The above reaction is a condensation reaction and can be conducted in a usual manner. Preferable results may generally be obtained if the reaction is carried out in the presence of a base such as pyridine, potassium carbonate or triethylamine while using acetone, DMF or the like as a solvent.

Certain Pharmacological Experiments will next be given to describe the effects of the present invention in more detail.

PHARMACOLOGICAL EXPERIMENT 1

Hypotensive effects in spontaneously hypertensive rats (SHR) under anesthesia

1. Method

Male SHR of 20 weeks of age or older were anesthetized with sodium pentobarbital (40 mg/kg, i.p.). The carotid artery and jugular vein were cannulated. Blood pressure was recorded from the carotid artery on a polygraph via a pressure transducer. Test compounds were dissolved in a solution containing 0.9% NaCl and 1% Tween 80 and administered either intravenously into the jugular vein or intraduodenally through a cannula inserted into the duodenum.

As a representative of this invention, compound A (8-hydroxy-2-nitrato-methyl-7-nitro-1,4-benzodioxane) was chosen.

2. Results

Figure 2:
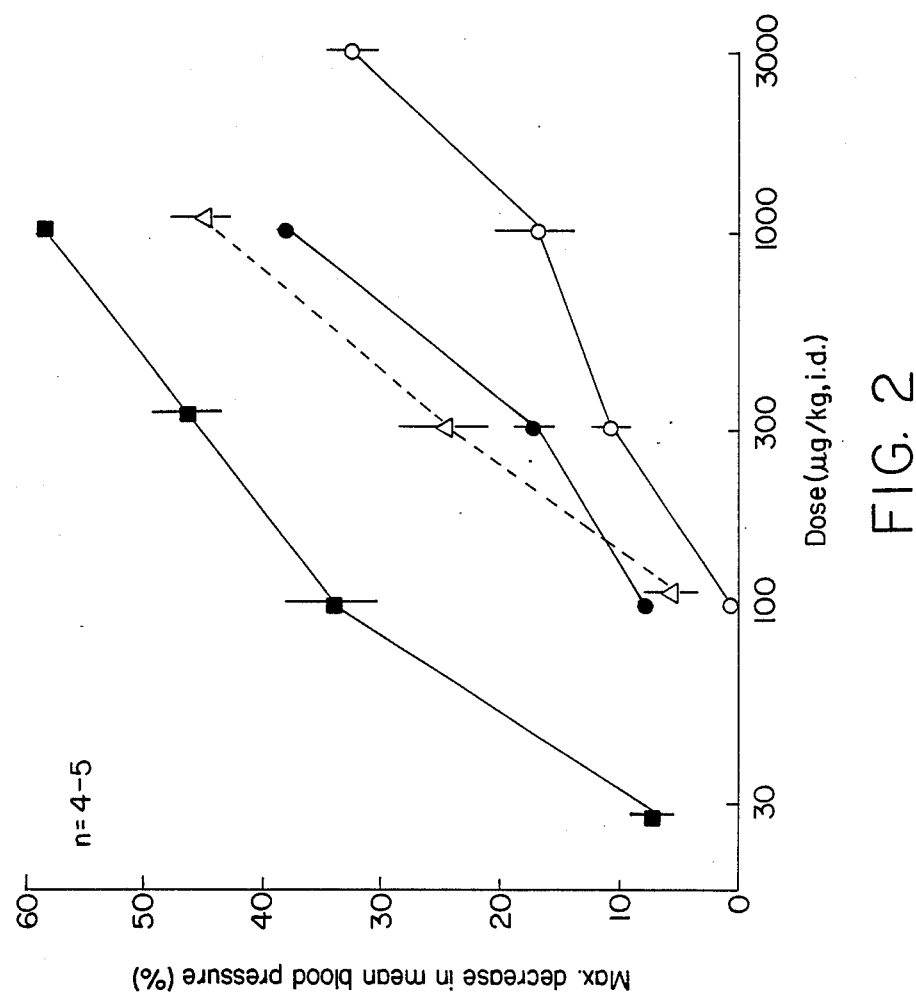

Results are shown in FIGS. 1 and 2.

FIG. 1 diagrammatically illustrates hypotensive effects in SHR under anesthesia, upon intravenous injection. Values are means ±s.e.m. (■: compound A, : NG, ●: ISDN, Δ: nicorandil). Letter n indicates the number of animals.

FIG. 2 diagrammatically depicts hypotensive effects in SHR under anesthesia, upon intraduodenal administration. Values are means ±s.e.m. (■: compound A, ●: NG, : ISDN, Δ: nicorandil). Letter n indicates the number of animals.

Compound A caused a marked hypotension after intravenous administration at a dose as small as 0.3 μg/kg.

The potency of compound A to cause 30% decrease in means aortic pressure was 5, 250 and 300 times larger than NG, ISDN and nicorandil (N-[2-(nitroxy)ethyl]-3-pyridinecarboxamide), respectively. Compound A also caused a dose-dependent hypotension after intraduodenal administration. The potency of compound A was about 5, 10 and 30 times larger than nicorandil, NG and ISDN, respectively.

PHARMACOLOGICAL EXPERIMENT 2

Effects on the arterial and venous systems in anesthetized open-chest dogs

1. Methods

Mongrel dogs of either sex, weighing 12–16 kg were subjected to inhalation anesthesia with enflurane under artificial respiration. The dogs were subjected to thoracotomy through the fourth right intercostal wall and catheters were inserted into the thoracic aorta and right pulmonary artery. The aortic and pulmonary blood pressures were measured by means of cathether tip-type piezoelectric transducers.

Test compounds were cumulatively administered with intervals of 30 minutes either intravenously or intraduodenally through catheters placed in the left femoral vein and duodenum.

2. Results

The results are summarized in Table 1.

TABLE 1

| Compound | Route | Dose (μg/Kg) | Number of animals | Max. change in mean blood pressure at diastole (mm/Hg) Aortic | Pulmonary |
|---|---|---|---|---|---|
| NG | i.v | 3 | 3 | −21.7 | −0.8 |
|  | i.v | 10 | 3 | −33.3 | −3.0 |
|  | i.v | 30 | 3 | −40.0 | −3.7 |
|  | i.d | 30 | 3 | −1.7 | −0.7 |
|  | i.d | 100 | 3 | −3.3 | −1 |
|  | i.d | 300 | 3 | −10 | −1.7 |
| ISDN | i.v | 30 | 3 | −2 | −2.5 |
|  | i.v | 100 | 3 | 0 | −2.8 |
|  | i.v | 300 | 3 | −6 | −3.8 |
|  | i.d | 30 | 3 | −5 | −0.7 |
|  | i.d | 100 | 3 | −6.7 | −0.7 |
|  | i.d | 300 | 3 | −5.8 | −1.7 |
| Nicorandil | i.v | 30 | 4 | −10.3 | −1 |
|  | i.v | 100 | 4 | −18.6 | −1.5 |
|  | i.v | 300 | 4 | −50.9 | −2.1 |
| Compound A | i.v | 1 | 3 | −23 | −2.5 |
|  | i.v | 3 | 3 | −39.2 | −3.2 |
|  | i.v | 10 | 3 | −44.2 | −5.3 |
|  | i.d | 30 | 3 | −2 | −1.5 |
|  | i.d | 100 | 3 | −15 | −2.5 |
|  | i.d | 300 | 3 | −22 | −3.5 |

After intravenous administration, compound A reduced aortic and pulmonary blood pressure dose-dependently. The vasodilating effects of compound A on the arterial and venous system as assessed from the reduction in aortic and pulmonary blood pressure respectively, was about 3 times more potent than those of nicorandil. The effect of ISDN on the aortic pressure was minimum at a dose-range 30 times larger than that of compound A.

Compound A also caused dose-dependent reductions in aortic and pulmonary blood pressures after intraduodenal administration. The potency of compound A was about 3 times larger than that of NG.

Pharmacological Experiment 3

Effects on the coronary blood flow in anesthetized open-chest dogs

1. Methods

Mongrel dogs of either sex weighing 9–14 kg were subjected to inhalation anesthesia with enflurane under artificial respiration. The dogs were subjected to thoracotomy through the fourth left intercostal wall and a magnetic flow meter prove was attached to the circumflex branch of the left coronary artery to measure the coronary blood flow. Test compounds were administered cumulatively at intervals of 10 minutes through a catheter inserted into the left femoral vein.

2. Results

Results are summarized in Table 2.

TABLE 2

| Compound | Dose (μg/Kg) | Number of animals | Max. increase in coronary blood flow (%) |
|---|---|---|---|
| NG | 3 | 3 | 31.3 |
|  | 10 | 3 | 79.7 |
|  | 30 | 3 | 165.0 |
| Sodium nitroprusside | 1 | 3 | 0 |
|  | 3 | 3 | 22.2 |
|  | 10 | 3 | 101.9 |
| Compound A | 1 | 3 | 52.0 |
|  | 3 | 3 | 84.7 |
|  | 10 | 3 | 127.6 |

Intravenous administration of compound A caused a marked and dose-dependent increase in coronary blood flow at a dose range as small as 1–10 μg/kg.

The effect of compound A on the coronary flow was about 3 times more potent than that of NG.

From the above-described results, it is clear that the compounds of this invention have strong vasodilative effects on the coronary and peripheral arteries as well as on the peripheral veins. This means that the compounds of this invention are useful as therapeutic compositions for ischemic heart diseases such as angina pectoris and cardiac infarction, and for cardiac failure.

The toxicity of the compounds of this invention will next be described.

Acute toxicity in mice was investigated with respect to 8-hydroxy-2-nitratomethyl-7-nitro-1,4-benzodioxane. Its $LD_{50}$ was 200–250 mg/kg at intravenous administration and 500–1,000 mg/kg at oral administration. A similar experiment was also conducted with an intravenous administration of NG. Its $LD_{50}$ was 10–15 mg/kg.

From the above results, it is clear that the compounds of this invention are extremely safer than NG. The present invention has an extremely high value for this advantage too.

As apparent from the results of the above-described Pharmacological Experiments, the compounds of this invention are effective as therapeutic and preventive compositions for ischemic heart diseases, typified by cardiac infarction and a variety of angina pectoris, and heart failure; for the control of blood pressure during a surgical operation; etc. They have superior effects compared with conventional nitro-containing agents and moreover, have higher safety than the conventional nitro-containing agents. Hence, the present invention has an extremely high value.

When the compounds of this invention are applied for the above-described objects, they are administered orally or parenterally (i.e., as injections or external preparations). Their dose varies depending on the type and severity of disease and age as well as whether there is an emergency situation or not. No specific limitation is therefore imposed on the dose. The dose may however be on the order of about 0.1–100 mg, preferably 0.5–40 mg, most preferably 1–20 mg per day for an adult. In the case of injections, each compound may be administered, for example, at a rate of about 0.1–5 mg/hour, preferably, about 0.5–3 mg/hour by intravenous drip infusion.

In order to form the compounds of this invention into suitable dosage forms, they may be made into such forms as tablets, granules, powders, capsules, injections, external preparations, suppositories, etc. in accordance with routine techniques employed in this field.

More specifically, for preparing a solid preparation for oral administration, the active ingredient is mixed with an excipient and, if necessary, a binder, disintegrator, lubricant, coloring agent, corrigent and the like, and then formed into tablets, coated tablets, granules, powders, capsules, etc. by methods known per se in the art.

Examples of the excipient may include lactose, corn starch, saccharose, glucose, sorbitol, crystalline cellulose, etc. On the other hand, illustrative binders may include polyvinyl alcohol, polyvinyl ether, ethylcellulose, methylcellulose, gum arabic, tragacanth gum, gelatin, shellac, hydroxypropylcellulose, hydroxypropylstarch, polyvinyl pyrrolidone and the like. As illustrative disintegrators, there may be mentioned starch, agar, gelatin powder, microcrystalline cellulose, calcium carbonate, sodium hydrogencarbonate, calcium citrate, dextrin, pectin, etc. Lubricants may include magnesium stearate, talc, polyethylene glycol, silica, hardened vegetable oil, etc. by way of example. Illustrative coloring agents may include those permitted for incorporation in medicines. As corrigents, use may be made of, for example, cocoa powder, menthol, aromatic acids, mentha oil, Borneo camphor, cinnamon powder, etc. These tablets and granules may of course be applied with sugar or gelatin coating or any other suitable coating as needed.

For preparing an injection, the active ingredient is added with a pH-adjusting agent, buffer, stabilizer, solubilizer, preservative and/or the like as needed, and then formed into a subcutaneous, intramuscular or intravenous injection by a method known per se in the art.

When a preparation suitable for intravenous drip infusion is desired, the injection may be used as is or alternatively, it may be diluted with a physiological saline or a glucose solution for use in intravenous drip infusion.

Examples of this invention will next be described. Needless to say, the present invention is by no means limited to them.

EXAMPLE 1

8-Hydroxy-2-nitratomethyl-7-nitro-1,4-benzodioxane

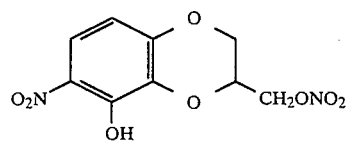

(1) Synthesis of 8-hydroxy-2-hydroxymethyl-1,4-benzodioxane

Pyrogallol (757 g; 6.0 moles), sodium sulfite (3 g), water (2.2 l) and anhydrous sodium borate (317 g; 1.58 moles) were charged in a 5-l 4-neck flask. The contents were stirred into a solution. After substituting the interior gas of the flask with argon, there were added with stirring at room temperature sodium iodide (30 g), sodium hydroxide (120 g; 3.0 moles) dissolved in water (300 ml) and epichlorohydrin (610 g; 6.6 moles). The resulting mixture was stirred for one day, followed by further addition of caustic soda (12 g; 0.3 mole) and epichlorohydrin (167 g; 1.8 moles). The contents were thereafter stirred at room temperature for 3 days. The reaction mixture was then washed twice with dichloromethane. While stirring the aqueous layer under ice-cooling, a mixture of caustic soda (800 g) and water (1.5 l) was added. The resulting mixture was then heated back to room temperature, at which it was stirred for 3 hours.

Concentrated sulfuric acid (1.4 l) was thereafter added the reaction mixture to lower its pH to about 8.0. The reaction mixture was then extracted three times with ethyl acetate. After washing the ethyl acetate layer twice with a saturated aqueous solution of $Na_2B_4O_7$ and then with a saturated saline, ethyl acetate was distilled off under reduced pressure. The resulting pale yellowish brown oil was subjected to silica gel chromatography (silica gel: about 2 kg; developer: chloroform-methanol) and then crystallized from chloroform-n-hexane, thereby obtaining 540 g of the title compound, i.e., 8-hydroxy-2-hydroxymethyl-1,4-benzodioxane (yield: about 50%) as colorless crystals.

Melting point (°C.): 98–102.

(2) Synthesis of 8-hydroxy-2-nitratomethyl-7-nitro-1,4-benzodioxane

8-Hydroxy-2-hydroxymethyl-1,4-benzodioxane (127.4 g; 0.7 mole) obtained by the procedure (1), urea (1.5 g) and acetonitrile (1 l) were charged in a 2-l 4-neck flask, to which acetyl nitrate [prepared from 99% fuming nitric acid (134 ml), acetic anhydride (375 g) and concentrated sulfuric acid (several drops) in acetonitrile] was added dropwise with cooling and stirring (internal temperature: about $-35°$ C.). About fifteen minutes later, a solution caustic soda (120 g) dissolved in water (240 ml) was carefully added dropwise at temperatures below $-30°$ C.

The reaction mixture was then poured in water (about 3 l). After stirring it overnight, the resulting deposit was collected by filtration and washed first with water and then with methanol. Hot methanol (500 ml) was added to the deposit. After stirring and cooling the resulting mixture, the resulting deposit was collected by filtration. Furthermore, hot chloroform (1.5 l) was added to the deposit and the resulting mixture was then filtered under heat to remove insoluble matter. The insoluble matter was extracted with hot chloroform (1 l) in the same manner. The extract was combined with the chloroform solution, followed by an addition of silica gel (about 200 g). After stirring the resulting mixture, it was filtered. Chloroform was then distilled off from the filtrate, and the residue was dissolved in hot acetone, followed by an addition of methanol. The deposited crystals were collected by filtration to obtain 58 g of the title compound, i.e., 8-hydroxy-2-nitratomethyl-7-nitro-1,4-benzodioxane (yield: 30%) as yellowish crystals.

Melting point (°C.): 160–162.

IR (Nujol ®)cm$^{-1}$: 1620, 1273 } (ONO$_2$)

| Elemental analysis for $C_9H_8N_2O_8$: | | | |
|---|---|---|---|
| | C | H | N |
| Calculated (%) | 39.71 | 2.96 | 10.29 |
| Found (%) | 39.73 | 2.88 | 10.31 |

EXAMPLE 2

8-Methoxy-2-nitratomethyl-7-nitro-1,4-benzodioxane

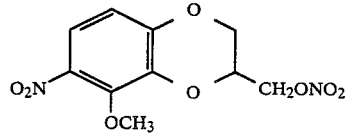

8-Hydroxy-2-nitratomethyl-7-nitro-1,4-benzodioxane (200 mg) obtained in Example 1 was dissolved in methanol (30 ml), followed by an excessive addition of an ether solution of diazomethane at room temperature. Thirty minutes later, the reaction mixture was concentrated under reduced pressure to dryness so that the title compound (220 mg) was obtained in an oily form. When it was left over in a refrigerator, it was solidified. Its melting point was 73°–74° C.

IR (Nujol ®)cm$^{-1}$: 1625, 1275 } (ONO$_2$)

| Elemental analysis for $C_{10}H_{10}N_2O_8$: | | | |
|---|---|---|---|
| | C | H | N |
| Calculated (%) | 41.96 | 3.52 | 9.79 |
| Found (%) | 42.13 | 3.60 | 9.65 |

EXAMPLE 3

8-Acetoxy-2-nitratomethyl-7-nitro-1,4-benzodioxane

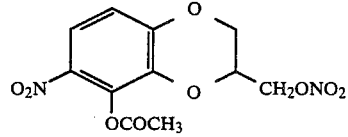

8-Hydroxy-2-nitratomethyl-7-nitro-1,4-benzodioxane (200 mg) obtained in Example 1 was dissolved in pyridine (5 ml), followed by an addition of acetic anhydride. The reaction mixture was heated to 80°–85° C. so as to conduct the intended reaction. The reaction mixture was then concentrated under reduced pressure to dryness, followed by recrystallization from methanol to obtain title compound (200 mg) as colorless needle-like crystals.

Melting point (°C.): 115–116

IR (Nujol ®)cm$^{-1}$: 1773 (\C=O/)

-continued $$\left.\begin{array}{l}1632\\1280\\1290\end{array}\right\} (ONO_2)$$

| Elemental analysis for $C_{11}H_{10}N_2O_9$: | | | |
|---|---|---|---|
| | C | H | N |
| Calculated (%) | 42.05 | 3.21 | 8.92 |

-continued

| Elemental analysis for $C_{11}H_{10}N_2O_9$: | | | |
|---|---|---|---|
| | C | H | N |
| Found (%) | 42.22 | 3.26 | 8.69 |

EXAMPLES 4-17

Following the procedures of Examples 1-3, various compounds were obtained as shown in the following Tables 3 and 4.

TABLE 3

| Example No. | Compound | Appearance m.p. (°C.) | IR cm⁻¹ | Molecular formula | Elemental analysis data Calculated/found | | |
|---|---|---|---|---|---|---|---|
| | | | | | C (%) | H (%) | N (%) |
| 4 | [structure: 4-nitro-2,3-(glycidyl)phenol sodium salt with CH₂ONO₂] | Reddish powder 150 - (decomp'd) | Nujol 1632, 1275 (ONO₂) | C₉H₇O₈N₂Na | 36.74 36.89 | 2.40 2.40 | 9.53 9.4 |
| 5 | [structure with nicotinate ester·HCl] | Pale yellowish powder 165 (decomp'd) | Nujol 1625, 1285 (ONO₂) 1708 (COO) | C₁₅H₁₁O₉N₃·HCl | 43.55 43.81 | 2.92 2.88 | 10.16 9.98 |
| 6 | [structure with O—C(O)—OC₂H₅] | Pale yellowish crystals 71-73 | Nujol 1636, 1295 (ONO₂) 1775 (OCOO) | C₁₂H₁₂O₁₀N₂ | 41.87 41.88 | 3.51 3.47 | 8.14 8.04 |
| 7 | [structure with O—(CH₂)₂—N-morpholine·HCl] | Colorless powder 147-149 (decomp'd) | Nujol 1633, 1273 (ONO₂) | C₁₅H₁₉O₉N₃·HCl | 42.71 42.83 | 4.78 4.88 | 9.96 9.78 |
| 8 | [structure with OH] | Pale brownish crystals 131-135 | Nujol 3440 (OH) 1620, 1277 (ONO₂) | C₉H₈O₈N₂ | 39.71 39.70 | 2.96 2.77 | 10.29 10.51 |
| 9 | [structure with OCH₃] | Pale yellowish needle-like crystals 78-82 | Nujol 1630, 1272 (ONO₂) | C₁₀H₁₀O₈N₂ | 41.96 42.18 | 3.52 3.29 | 9.79 9.76 |

TABLE 3-continued

| Example No. | Compound | Appearance m.p. (°C.) | IR cm$^{-1}$ | Molecular formula | Elemental analysis data Calculated/found C (%) | H (%) | N (%) |
|---|---|---|---|---|---|---|---|
| 10 | 3-nitro-2-(acetyloxy)phenyl glycidyl derivative with CH$_2$ONO$_2$ (structure: benzene ring with NO$_2$, O-CH$_2$-CH(CH$_2$ONO$_2$)-O, OC(=O)CH$_3$) | Pale yellowish oil | Liquid film 1632, 1273 (ONO$_2$); 1768 (COO) | C$_{11}$H$_{10}$O$_9$N$_2$ | 42.05 / 41.89 | 3.21 / 3.08 | 8.92 / 9.03 |
| 11 | Benzene ring with OH, fused dioxane bearing CH$_2$ONO$_2$ | Colorless oil | Liquid film 3500 (OH); 1623, 1270 (ONO$_2$) | C$_9$H$_9$O$_6$N | 47.58 / 47.72 | 3.99 / 3.88 | 6.17 / 6.01 |
| 12 | Benzene with OCH$_3$, fused dioxane bearing CH$_2$ONO$_2$ | Colorless crystals 40–47 | Liquid film 1625, 1270 (ONO$_2$) | C$_{10}$H$_{11}$O$_6$N | 49.79 / 49.58 | 4.60 / 4.48 | 5.81 / 5.99 |
| 13 | Benzene with OCH$_3$, fused dioxane bearing CH$_2$ONO$_2$ (isomer) | Colorless oil | Liquid film 3500 (OH); 1625, 1270 (ONO$_2$) | C$_9$H$_9$O$_6$N | 47.58 / 47.81 | 3.99 / 4.15 | 6.17 / 5.89 |
| 14 | Benzene with OCH$_3$, fused dioxane bearing CH$_2$ONO$_2$ (isomer) | Colorless oil | Liquid film 1620, 1270 (ONO$_2$) | C$_{10}$H$_{11}$O$_6$N | 49.79 / 49.91 | 4.60 / 4.46 | 5.81 / 5.66 |
| 15 | Benzene with NO$_2$ and OCH$_3$, fused dioxane bearing CH$_2$ONO$_2$ | Pale yellowish needle-like crystals 172–173.5 | Nujol 1610, 1280 (ONO$_2$) | C$_{10}$H$_{10}$O$_8$N$_2$ | 41.96 / 41.87 | 3.52 / 3.52 | 9.79 / 9.80 |
| 16 | Benzene with NO$_2$, NO$_2$, OH, fused dioxane bearing CH$_2$ONO$_2$ | Yellowish prismatic crystals 151–152.5 | Nujol 1632, 1270 (ONO$_2$) | C$_9$H$_7$O$_{10}$N$_3$ | 34.08 / 33.97 | 2.23 / 2.41 | 13.24 / 13.50 |
| 17 | Benzene with NO$_2$, fused dioxane bearing CH$_2$ONO$_2$ | Colorless powder 60–62 | Nujol 1625, 1270 (ONO$_2$) | C$_9$H$_8$O$_7$N$_2$ | 42.19 / 42.28 | 3.15 / 3.21 | 10.94 / 10.86 |

TABLE 4

| Example No. | Compound | Appearance m.p. (°C.) | IR cm$^{-1}$ | Molecular formula | Elemental analysis data Calculated/found C (%) | H (%) | N (%) |
|---|---|---|---|---|---|---|---|
| 18 | [structure: benzene ring with O₂N, OH substituents and dioxane ring with CH₂ONO₂] | Yellowish crystals 96–98.5 | Nujol 1630 ⎞ ONO₂ 1270 ⎠ | $C_9H_8O_8N_2$ | 39.71 / 39.86 | 2.96 / 2.90 | 10.29 / 10.31 |
| 19 | [structure: CN, OAc substituted benzene fused dioxane with CH₂ONO₂] | Pale yellowish crystals 67.5–68.5 | Liquid film 2205 (CN) 1630 ⎞ (ONO₂) 1270 ⎠ 1760 (COO) | $C_{12}H_{10}O_7N_2$ | 48.99 / 48.89 | 3.43 / 3.41 | 9.52 / 9.52 |
| 20 | [structure: CN, OH substituted benzene fused dioxane with CH₂ONO₂] | Colorless needle-like crystals 111–116 (133–134) (Double melting point) | Nujol 3250 (OH) 2215 (CN) 1630 ⎞ (ONO₂) 1280 ⎠ | $C_{10}H_8O_6N_2$ | 47.62 / 47.44 | 3.20 / 3.14 | 11.11 / 10.96 |
| 21 | [structure: CN, O₂N, OH substituted benzene fused dioxane with CH₂ONO₂] | Yellowish crystals 150–152 | Nujol 2220 (CN) 1638 ⎞ ONO₂ 1275 ⎠ | $C_{10}H_7O_8N_3 \cdot \frac{1}{2}H_2O$ | 39.60 / 39.87 | 2.53 / 2.31 | 13.86 / 13.88 |
| 22 | [structure: COOH, O₂N, OH substituted benzene fused dioxane with CH₂ONO₂] | Yellowish crystals 192–194 (decomp'd) | Nujol 1630 ⎞ ONO₂ 1280 ⎠ 1685 (COOH) | $C_{10}H_8O_{10}N_2$ | 37.98 / 38.01 | 2.55 / 2.53 | 8.86 / 8.87 |
| 23 | [structure: NC, OCH₃ substituted benzene fused dioxane with CH₂ONO₂] | Colorless crystals 97.5–98 | Nujol 2202 (CN) 1635 ⎞ (ONO₂) 1272 ⎠ | $C_{11}H_{10}O_6N_2$ | 49.63 / 49.59 | 3.79 / 3.75 | 10.52 / 10.77 |
| 24 | [structure: NC, OH substituted benzene fused dioxane with CH₂ONO₂] | Colorless crystals 160–162 | Nujol 3230 (OH) 2210 (CN) 1623 ⎞ (ONO₂) 1272 ⎠ | $C_{10}H_8O_6N_2$ | 47.62 / 47.81 | 3.20 / 3.17 | 11.11 / 10.65 |
| 25 | [structure: HOOC, OCH₃ substituted benzene fused dioxane with CH₂ONO₂] | Colorless crystals 132–134 | Nujol 1620 ⎞ (ONO₂) 1272 ⎠ 1668 (COOH) | $C_{11}H_{11}O_8N$ | 46.32 / 46.44 | 3.89 / 3.78 | 4.91 / 4.77 |
| 26 | [structure: HOOC, OH substituted benzene fused dioxane with CH₂ONO₂] | Colorless needle-like crystals 217–218 (decomp'd) | Nujol 1610 ⎞ (ONO₂) 1285 ⎠ 1642 (COOH) | $C_{10}H_9O_8N$ | 44.29 / 44.29 | 3.35 / 3.30 | 5.17 / 5.04 |

TABLE 4-continued

| Example No. | Compound | Appearance m. p. (°C.) | IR cm$^{-1}$ | Molecular formula | Elemental analysis data Calculated/found | | |
|---|---|---|---|---|---|---|---|
| | | | | | C (%) | H (%) | N (%) |
| 27 | 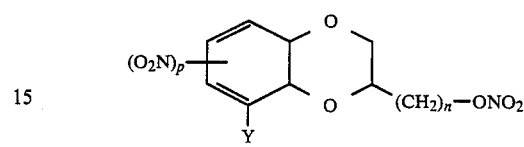 | Colorless oil | Liquid film 1630 } (ONO$_2$) 1270 1710 (COOCH$_3$) | C$_{12}$H$_{13}$O$_8$N | 48.16 47.87 | 4.38 4.26 | 4.68 4.80 |

What is claimed is:

1. A 1,4-benzodioxane derivative represented by the following formula:

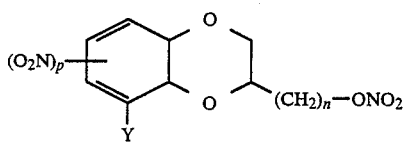

wherein p stands for an integer of 0–2, Y represents a hydrogen atom; or a group represented by the formula —OR in which R denotes a hydrogen atom, a lower alkyl, lower alkoxycarbonyl an alkanoyl, nicotinoyl, or a group represented by the formula

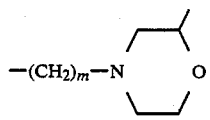

in which m is 1 or 2; n is an integer of 1–3, exclusive of the case wherein p=0 and Y=H, or a pharmacologically acceptable salt thereof.

2. The 1,4-benzodioxane derivative or a pharmacologically acceptable salt thereof as claimed in claim 1, wherein n is 1.

3. The 1,4-benzodioxane derivative or a pharmacologically acceptable salt thereof as claimed in claim 1, wherein p=n=1.

4. The 1,4-benzodioxane derivative or a pharmacologically acceptable salt thereof as claimed in claim 1, wherein p is 2.

5. The 1,4-benzodioxane derivative or a pharmacologically acceptable salt thereof as claimed in claim 1, wherein Y is a hydroxyl group.

6. The 1,4-benzodioxane derivative or a pharmacologically acceptable salt thereof as claimed in claim 1, wherein n and p individually represent 1, Y represents a hydroxyl group, and the nitro group is bonded to the 7-position.

7. A pharmaceutical composition for ischemic heart disease, comprising an effective amount for the treatment of such disease of a 1,4-benzodioxane derivative represented by the following formula:

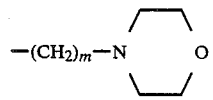

wherein p stands for an integer of 0–2, Y represents a hydrogen atom; or a group represented by the formula —OR in which R denotes a hydrogen atom, a lower alkyl, lower alkoxycarbonyl, an alkanoyl, nicotinoyl, or a group represented by the formula

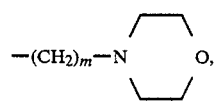

in which m is 1 or 2; n is an integer of 1–3, exclusive of the case wherein p=0 and Y=H, or a pharmacologically acceptable salt thereof and a pharmacologically acceptable carrier.

8. The pharmacological composition as claimed in claim 7, comprising as an effective ingredient a compound wherein p=1, m=1, and Y=OH, or a pharmacologically acceptable salt thereof.

9. The pharmacological composition as claimed in claim 7, comprising, as an effective ingredient, 8-hydroxy-2-nitratomethyl-7-nitro-1,4-benzodioxane or a pharmacologically acceptable salt thereof.

10. A method for the treatment of ischemic heart disease which comprises administering to a patient suffering from the said disease a therapeutically effective amount of a 1,4-benzodioxane derivative represented by the following formula:

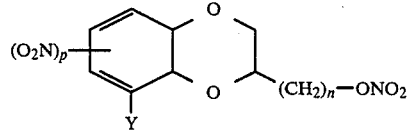

wherein p represents an integer of 0 to 2, Y represents hydrogen atom; or a group represented by the formula —OR in which R denotes hydrogen atom, a lower alkyl, lower alkoxycarbonyl, an alkanoyl, nicotinoyl, or a group represented by the formula —(CH$_2$)$_m$—N   O, in which m is 1 or 2; n is an integer of 1 to 3, exclusive of the case wherein p=0 and Y=H, or a pharmacologically acceptable salt thereof.

* * * * *